US00PP07823P

United States Patent [19]

Dupont et al.

[11] Patent Number: Plant 7,823

[45] Date of Patent: Mar. 10, 1992

[54] DWARF COREOPSIS VARIETY NAMED *COREOPSIS GRANDIFLORA* 'SUNDANCER'

[75] Inventors: Robert J. Dupont; Robert J. Dupont, Jr., both of Plaquemine, La.

[73] Assignee: Dupont's Nursery, Plaquemine, La.

[21] Appl. No.: 552,001

[22] Filed: Jul. 12, 1990

[51] Int. Cl.[5] ..... A01H 5/00

[52] U.S. Cl. ..... Plt./68

[58] Field of Search ..... Plt./68

[56] References Cited

PUBLICATIONS

Anon., "*The Seed Catalogue*" printed by Thompson and Morgan, P.O. Box 308, Jackson, N.J. 08527, 1986, p. 57.

Pettingill, A. "Coreopsis", *The White-Flower-Farm Garden Book*, 1977, Little, Brown and Co., Boston, p. 102.

*Primary Examiner*—James R. Feyrer

*Attorney, Agent, or Firm*—Reginald F. Roberts, Jr.

[57] ABSTRACT

A new and distinct cultivar of *Coreopsis grandiflora* Haag ez Sweet, resulting from a selection of a crop of seedlings of *Coreopsis grandiflora* 'Sunray', characterized by its exceptional dwarfism, its unique spreading habit, and its early blooming.

1 Drawing Sheet

BACKGROUND OF THE INVENTION

The present invention relates to a new and distinct cultivar of *Coreopsis grandiflora* Haag es Sweet, resulting from a selection of a seedling of *Coreopsis grandiflora* 'Sunray.' Applicants have asexually reproduced the plant by stem cuttings.

SUMMARY OF THE INVENTION

The primary features of this new variety which connote its distinctive advance over existing types are: (a) its exceptional dwarfism, the height of the plant being from about fifteen to about twenty centimeters; (b) double blossoms, about five centimeters in diameter; (c) blooms almost continuously throughout the year in the South, without the pinching of spent blooms; and (d) its spreading habit, forming masses up to one hundred centimeters in width.

BRIEF DESCRIPTION OF THE DRAWING

The single drawing (the FIGURE) is a photograph of the plant claimed by applicants.

BOTANICAL DESCRIPTION OF THE PLANT

The following constitutes a detailed description of the new variety, the plant being illustrated by the accompanying photograph of a specimen thereof in natural color.

Type: Hardy, herbaceous perennial.

Propagation: Reproduced by vegetative propagation only; holds its distinctive character through successive propagations. Seed produced is not viable.

Flowers: Borne solitary on long, naked peduncles ranging from four to sixteen centimeters in length. Double blooms are five centimeters in diameter. Disk and ray flowers are present with color and form identical to parent variety. All flower parts are present and seeds are formed, but their size is about two millimeters and they appear unexpanded, whereas seed of 'Sunray' is about four millimeters long and much fatter. Otherwise seed shape is same as for 'Sunray'.

Stems: Usually several, fifteen to twenty-five centimeters in length; glabrous, or, especially near the base, spreading-villous, leafy below subnaked and elongated above. Internode lengths from one half to eight centimeters.

Leaves: Spatulate to linear or lance-linear, simple or with one or two pairs of small lateral lobes, glabrous to villous or hirsute, the lower long-petiolate, up to fifteen centimeters long including petioles and two centimeters wide, the others reduced and sessile or nearly so. Foliage color is the same as parent variety.

Growth: Dwarf, spreading without the use of growth retardents, stems become prostrate as they lengthen, often rooting at the nodes, with terminals remaining upright. 'Sunray' and others of the species remain more nearly entirely upright.

Hardiness: Survived five degrees Fahrenheit temperature at Plaquemine, La. in December of 1989.

*Coreopsis grandiflora* 'Sundancer' has a more dwarf habit than any other cultivar of *Coreopsis grandiflora* with double blossoms, including the parent variety 'Sunray'. It blooms almost continuously throughout the year in the South, whereas the parent variety has a much more limited period of bloom. In spreading, 'Sundancer' forms horizontal masses up to one-hundred centimeters in width, whereas the masses formed by 'Sunray' are much narrower and more nearly upright or vertical. In spreading, the stems of 'Sundancer' become prostrate as they lengthen, whereas those of 'Sunray' remain nearly upright. In contrast with 'Sunray', the parent variety, 'Sundancer' is characterized with double blossoms about five centimeters in diameter, whereas those of 'Sunray' are much larger. Seeds of 'Sundancer' are about two millimeters and unexpanded; seeds of 'Sunray' are about four millimeters long and much fatter.

We claim:

1. A new and distinct cultivar of *Coreopsis grandiflora*, characterized as to novelty by its exceptional dwarfism coupled with double flower, its unique spreading habit, and its early and continuous blooming, substantially as shown and described.

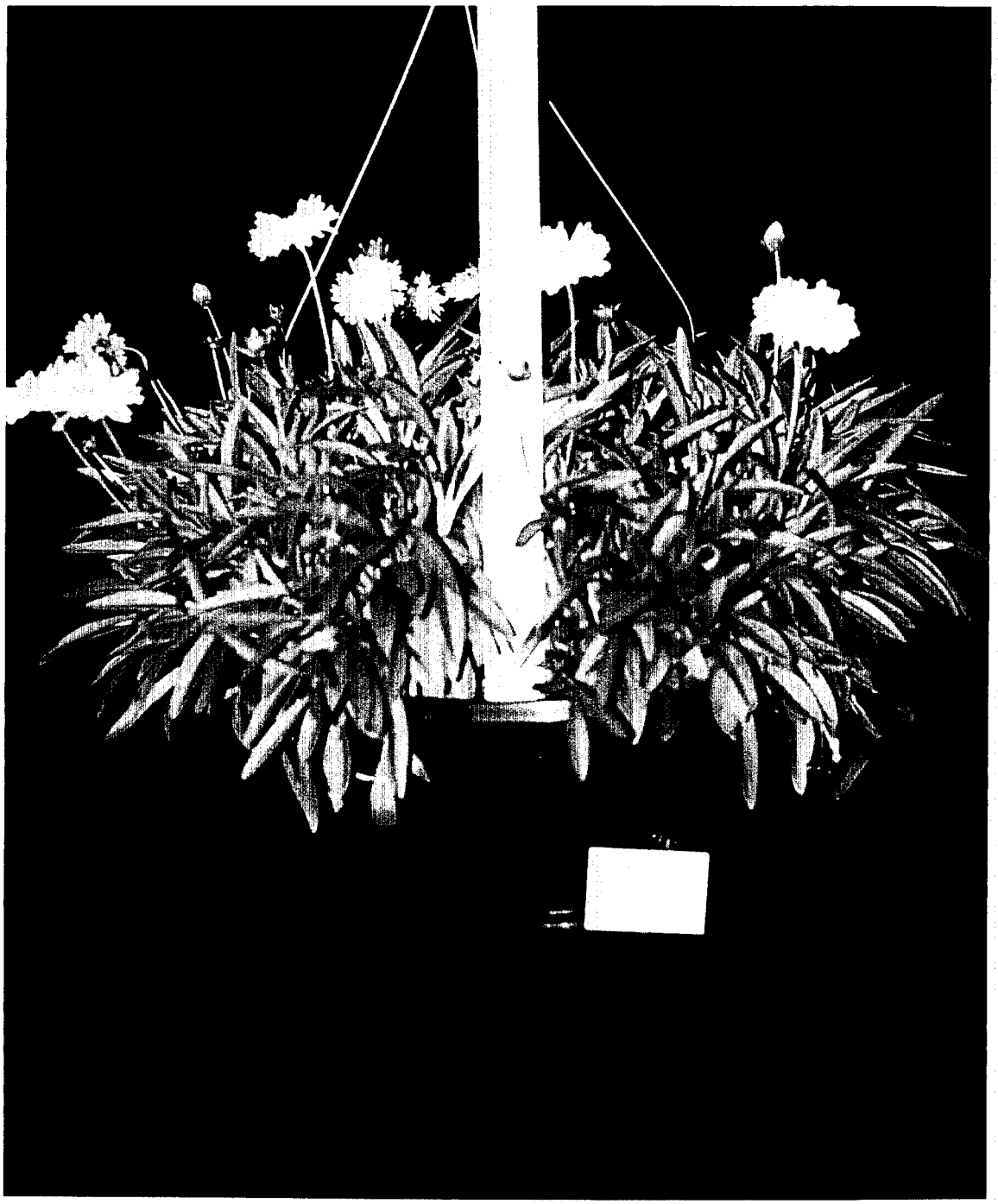

* * * * *